United States Patent [19]

Miripol et al.

[11] Patent Number: 4,704,352
[45] Date of Patent: Nov. 3, 1987

[54] L-ASCORBATE-2-PHOSPHATE SALTS IN BLOOD CELL STORAGE

[75] Inventors: Jeffrey E. Miripol, Evanston, Ill.; Andrew Heaton, Norfolk, Va.; Richard L. Kandler, McHenry, Ill.

[73] Assignee: Baxter Travenol Laboratories, Inc., Deerfield, Ill.

[21] Appl. No.: 748,513

[22] Filed: Jun. 25, 1985

[51] Int. Cl.$^4$ ............................................. A01N 1/02
[52] U.S. Cl. ........................................ 435/2; 422/40; 436/8; 436/18; 436/826
[58] Field of Search .............. 514/475; 435/2; 422/40, 422/41; 436/8, 18, 103, 826; 424/101; 604/410

[56] References Cited

U.S. PATENT DOCUMENTS

| | | | |
|---|---|---|---|
| 3,328,255 | 6/1967 | Ilg | 167/78 |
| 3,347,745 | 10/1967 | Rinfret et al. | 167/74 |
| 3,658,848 | 4/1972 | Nomura et al. | 260/343.7 |
| 3,795,581 | 3/1974 | Deindoerfer et al. | 195/1.8 |
| 3,847,738 | 11/1974 | Brake et al. | 195/1.8 |
| 3,874,384 | 4/1975 | Deindoerfer et al. | 128/272 |
| 4,151,178 | 4/1979 | Seib et al. | 260/343.7 |
| 4,179,445 | 12/1979 | Sieb et al. | 549/222 |
| 4,267,269 | 5/1981 | Grode et al. | 435/2 |
| 4,314,025 | 2/1982 | McCue | 435/2 |
| 4,356,172 | 10/1982 | Nakao et al. | 424/101 |
| 4,476,221 | 10/1984 | Kane et al. | 435/2 |
| 4,609,372 | 9/1986 | Carmen et al. | 604/262 |

FOREIGN PATENT DOCUMENTS

| | | | |
|---|---|---|---|
| 0142002 | 5/1985 | European Pat. Off. | |
| 8303830 | 11/1983 | PCT Int'l Appl. | 424/101 |
| 488784 | 5/1937 | United Kingdom | 514/474 |
| 1054698 | 1/1967 | United Kingdom | 514/474 |
| 143029 | 1/1960 | U.S.S.R. | 514/474 |

OTHER PUBLICATIONS

Tao et al., Chem. Abstr. #180436f, vol. 97, p. 648, 1982.
Chemical Abstracts, vol. 101, 1984, 106959P, entitled Purification of L-Ascorbic Acid 2-Phosphate Ester.
Data sheet from Takeda.

Primary Examiner—Barry S. Richman
Assistant Examiner—C. M. Delahunty
Attorney, Agent, or Firm—Paul C. Flattery; Garrettson Ellis; Bradford R. L. Price

[57] ABSTRACT

A solution for blood cell storage having sugar-containing blood cell nutrients therein and additionally containing a magnesium or calcium L-ascorbate-2-phosphate salt is taught. The magnesium and calcium L-ascorbate-2-phosphate salts remain stable below pH 7 and thus permit sterilization of the solution at a pH at which degradation of both the L-ascorbate-2-phosphate salt and the nutrient sugar present in the solution is substantially avoided.

12 Claims, No Drawings

L-ASCORBATE-2-PHOSPHATE SALTS IN BLOOD CELL STORAGE

TECHNICAL FIELD

In the article of G. L. Moore, et al. entitled Improved Red Blood Cell Storage Using Optional Additive Systems (OAS) Containing Adenine, Glucose, and Ascorbate-2-Phosphate; *Transfusion* Vol. 21, No. 6, pp. 723-731 (1981), the use of sodium-L-ascorbate-2-phosphate as a component for blood cell storage solutions is disclosed. See particularly page 730. Such a material may be utilized by red blood cells during storage under conventional conditions to provide improved 2,3-DPG maintenance during and after the storage period which improves the cells' oxygen transport.

However, sodium L-ascorbate-2-phosphate is not very stable in the presence of autoclave sterilization temperatures (about 110°-122° C.), which of course is a necessary procedure for preparing a container with a red cell storage solution therein, so that red cells can be safely stored without sepsis. Specifically, sodium L-ascorbate-2-phosphate tends to degrade during a conventional autoclave sterilization cycle, unless the pH of the solution in which it resides is over 6. However, at such pHs which are over 6, sugars in the solution such as glucose tend to be unstable during an autoclave cycle, forming a colored material (caramelization).

Thus, it is very difficult indeed to make use of sodium L-ascorbate-2-phosphate in an otherwise typical red blood cell storage solution, since those solutions generally contain sugar as an energy source for the red blood cells. Since it is generally mandatory to provide autoclave sterilization of containers which carry an amount of red cell storage solution prior to placing red cells in the container, systems which attempt to make use of sodium L-ascorbate-2-phosphate necessarily exhibit serious drawbacks.

The compound magnesium L-ascorbate-2-phosphate is a known material, being commercially available. While the compound is soluble in water, current evidence indicates that the ascorbate-phosphate and the magnesium ions do not disassociate in solution. Thus, without wishing to be limited by theory, it appears that the typical molecule in solution may be a dimer, having three magnesium atoms, and a theoretical structure of magnesium-L-ascorbate-2-phosphate in solution of:

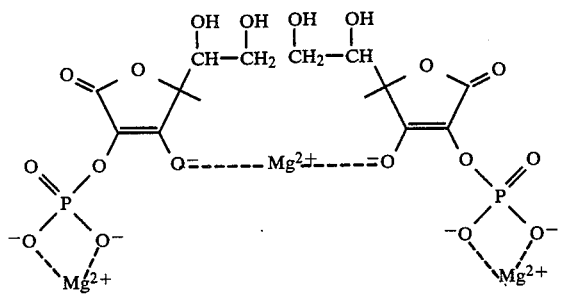

While the material shown may be hydrated, the compound may also be anhydrous, or provided with greater or lesser amounts of bonded or absorbed water.

DESCRIPTION OF THE INVENTION

In accordance with this invention, a solution for storing blood is provided in which the solution may be a typically conventional blood cell storage solution either provided in the original collection unit, or as an additive solution for later addition to red cells. The solution contains generally from 3 to 60 millimoles of magnesium L-ascorbate-2-phosphate per liter of solution, or an equal amount of the calcium analog thereof.

Significant advantages are achieved by the use of this material in blood cell storage solutions. Magnesium L-ascorbate-2-phosphate is more stable to steam sterilization conditions than the corresponding sodium salt, or free ascorbic acid. Nevertheless, it yields substantially equivalent 2,3-DPG maintenance in red blood cell storage to ascorbic acid and its sodium L-ascorbate-2-phosphate analog.

Furthermore, magnesium L-ascorbate-2-phosphate (hereafter "magnesium salt") is stable at pH of less than 7 (e.g. 4 to 7), so that the concentration of the magnesium salt in red cell storage solution may be diminished by no more than about 5 percent during a typical autoclaving, and also improved shelf life is obtained. This, in turn, permits the stabilization of glucose or equivalent sugars, since the solution may have a pH of less than 7 and preferably about pH 5 to 6.

For calculation of millimoles, the molecular weight of the magnesium salt is assumed to be 289. The calcium equivalent varies proportionately in its molecular weight.

Accordingly, after autoclaving, a sterile red cell storage solution may be provided which contains the magnesium salt with little degradation, and also which contains essentially undegraded sugar, without the undesired, colored materials which are typically formed by exposing glucose or the like to autoclaving conditions at a pH higher than 6 or 7.

The corresponding calcium L-ascorbate-2-phosphate may be used as a partial or complete substitute for the magnesium salt described above, to achieve similar advantages.

The magnesium salt, or its calcium salt equivalent (calcium L-ascorbate-2-phosphate) may be used in known red cell storage solutions such as ACD, CPD, or adenine solutions. Adenine solution is a product sold by Travenol Laboratories Inc. of Deerfield, Ill., under the registered trademark "ADSOL", being defined herein as an aqueous cell storage solution which contains, per 100 ml. of solution, essentially from 5 to 50 mg. of adenine, from 1,000 to 3,500 mg. of dextrose or fructose, from 400 to 1,200 mg. of sodium chloride, and from 250 to 2,000 mg. of mannitol, as described in U.S. Pat. No. 4,267,269.

Preferably, the magnesium or calcium salt is present in a concentration of 5 to 20 millimoles per liter of Adenine solution, or alternatively another red cell storage or collection solution.

From 50 to 250 ml. of red cell storage solution may be provided in a conventional blood bag for receiving one blood unit. After autoclaving the bag, the blood may be delivered into the bag and mixed with the red cell storage solution. Alternatively, previously collected packed red cells may be suspended for storage in the solution of this invention; i.e. by either adding the solution to the red cells, or by adding the red cells to the solution. One unit of packed red cells may be suspended in typically 75 to 150 ml. of solution. One unit of whole blood is of typically 513±50 ml. volume, while one unit of packed red cells at an 85% hematocrit is typically 223±30 ml. volume.

Long term storage of the red cells, either in the original plasma or preferably as suspended packed red cells, at 4° C. under conventional storage conditions, may then take place for a substantial length of time, for example 35 days, with the red cells exhibiting improved function in accordance with this invention.

It may also be desirable for the solution of this invention to contain other materials, for example inosine, guanosine, adenosine or another appropriate purine to provide to the solution an improved capacity for restoration or rejuvenation of 2,3-DPG and ATP in red blood cells after storage.

Further in accordance with this invention, one or more L-ascorbate-2-phosphate salts of sodium, potassium, magnesium or calcium may be added to the known Adenine solution of a formula as described above. Not only does such a mixture provide improved 2,3-DPG maintenance for red blood cells during their storage period, but, unexpectedly, reduce hemolysis of the blood cells has been noted, when compared with corresponding blood cells stored exclusively in Adenine solution.

For the reasons mentioned above, it is preferred to use the magnesium salt, or alternatively, the calcium salt of the L-ascorbate-2-phosphate.

As an added advantage of solutions of this invention, magnesium or calcium is provided to the stored cells, magnesium being of a valuable cofactor, and calcium being also used in cell growth and metabolism.

The above disclosure and the example below are offered for illustrative purposes, and are not intended to limit the scope of the invention of this application, which is defined in the claims below.

EXAMPLE 1

Solution containing the following, per 100 ml. of solution, was prepared:

| | |
|---|---|
| 2000 mg. | dextrose anhydrous |
| 900 mg. | sodium chloride |
| 750 mg. | mannitol |
| 27 mg. | adenine |
| 220 mg. | magnesium L-ascorbate-2-phosphate |
| balance | water |
| pH | 5.2 to 6.8 |

One hundred ml. of the above solution were placed into a Fenwal blood bag and sealed therein. The bag was then sterilized at 238° F. for 45 minutes at a pressure of 29 p.s.i.g. The bag was then pasteurized, after label application, at 182° F. for 60 minutes at a pressure of 8.5 p.s.i.g., and then at 170° F. for 3 hours at a pressure of 8.5 p.s.i.g.

No discoloration due to dextrose degradation was noted. Also, the solution was analyzed, and it was determined that the typical loss of magnesium L-ascorbate-2-phosphate was about two percent.

EXAMPLE 2

The experiment of Example 1 was repeated, except that the amount of magnesium L-ascorbate-2-phosphate per 100 ml. of solution was 438 mg. After sterilization and pasteurization, the loss of magnesium salt was essentially four percent. No discoloration was noted.

That which is claimed is:

1. In an aqueous solution for stabilizing blood during storage, which has therein a sugar-containing blood cell nutrient material, the improvement comprising in combination: from 3 to 60 millimoles of a material selected from the group consisting of magnesium L-ascorbate-2-phosphate and calcium L-ascorbate-2-phosphate per liter of solution.

2. The solution of claim 1 in which the pH is less than 7.

3. The solution of claim 1 in which from 5 to 20 millimoles of said material are present per liter of solution.

4. The solution of claim 1 in which said material is magnesium L-ascorbate-2-phosphate.

5. In an aqueous solution for stabilizing blood during storage, which has therein a sugar-containing blood cell nutrient material, the improvement comprising in combination: from 5 to 20 millimoles of magnesium L-ascorbate-2-phosphate per liter of solution, said solution having a pH of less than 7.

6. The solution of claim 5 wherein said solution further contains, per 100 ml of solution, from 5 to 50 mg. of adenine, from 1,000 to 3,500 mg. of dextrose, from 400 to 1,200 mg. of sodium chloride, and from 250 to 2,000 mg. of mannitol.

7. In an aqueous solution for stabilizing blood during storage, which contains, per 100 ml. solution, essentially from 5 to 50 mg. of adenine, from 1,000 to 3,500 mg. of sugar selected from the group consisting of dextrose and fructose, from 400 to 1,200 mg. of sodium chloride, and from 250 to 2,000 mg. of mannitol, the improvement comprising, in combination: from 3 to 60 millimoles of material selected from the group consisting of magnesium L-ascorbate-2-phosphate and calcium L-ascorbate-2-phosphate per liter of solution.

8. The solution of claim 7 in which the pH is in the range of 4 to 7.

9. The solution of claim 8 in which from 5 to 20 millimoles of said material are present per liter of solution.

10. The solution of claim 9 in which said material is magnesium L-ascorbate-2-phosphate.

11. The solution of claim 10 in which from 5 to 20 millimoles of magnesium L-ascorbate-2-phosphate are present per liter of solution and said solution has a pH in the range of 5 to 6.

12. The solution of claim 11 wherein said solution contains from 1,000 to 3,500 mg. of dextrose.

* * * * *